(12) United States Patent
Staal

(10) Patent No.: US 6,749,918 B2
(45) Date of Patent: *Jun. 15, 2004

(54) HYGIENE MATS

(76) Inventor: Johan Staal, Hammerweg 39, 7731 Ah Ommen (NL)

(*) Notice: Subject to any disclaimer, the term of this patent is extended or adjusted under 35 U.S.C. 154(b) by 111 days.

This patent is subject to a terminal disclaimer.

(21) Appl. No.: 09/900,972

(22) Filed: Jul. 10, 2001

(65) Prior Publication Data

US 2002/0031634 A1 Mar. 14, 2002

Related U.S. Application Data

(63) Continuation-in-part of application No. 09/195,450, filed on Nov. 18, 1998, now Pat. No. 6,258,435.

(30) Foreign Application Priority Data

Nov. 18, 1997 (NL) .............................. 1007566

(51) Int. Cl.[7] ................................. B32B 5/18
(52) U.S. Cl. .................... 428/71; 15/104.93; 15/215; 15/217; 428/76; 442/221; 442/287
(58) Field of Search ................... 442/221, 287; 428/71, 76, 95, 319.9; 15/104.92, 104.93, 215, 216, 217; D6/583

(56) References Cited

U.S. PATENT DOCUMENTS

| | | |
|---|---|---|
| 2,989,965 A | 6/1961 | Rod |
| 3,083,393 A | 4/1963 | Nappi |
| 5,164,164 A | 11/1992 | Strickler et al. |
| 5,792,712 A | 8/1998 | Hori et al. |
| 6,027,777 A | 2/2000 | Hirano et al. |
| 6,258,435 B1 * | 7/2001 | Staal ..................... 428/71 |

FOREIGN PATENT DOCUMENTS

| | | |
|---|---|---|
| DE | 84 563 | 5/1895 |
| DE | 26 39 289 | 3/1978 |
| EP | 0 060 148 | 9/1982 |
| FR | 2 761 255 | 10/1998 |
| GB | 2 268 399 | 1/1994 |
| NL | 69 03 255 | 12/1969 |

* cited by examiner

Primary Examiner—Ula Ruddock
Assistant Examiner—Jennifer Boyd
(74) Attorney, Agent, or Firm—Young & Thompson

(57) ABSTRACT

A mat provides for cleaning and disinfection of the soles of boots or shoes worn by humans, hooves of animals, and/or tires of automobiles or farm equipment. The mat includes a core which can retain a liquid, a permeable material surrounding the core, and a waterproof sleeve covering a bottom, sides, and part of a top of the core. When pressure is put on the mat, a depression is formed which bathes the depressing element in the liquid, while the waterproof sleeve prevents the liquid from overflowing.

5 Claims, 7 Drawing Sheets

HYGIENE MATS

Figure 1A:
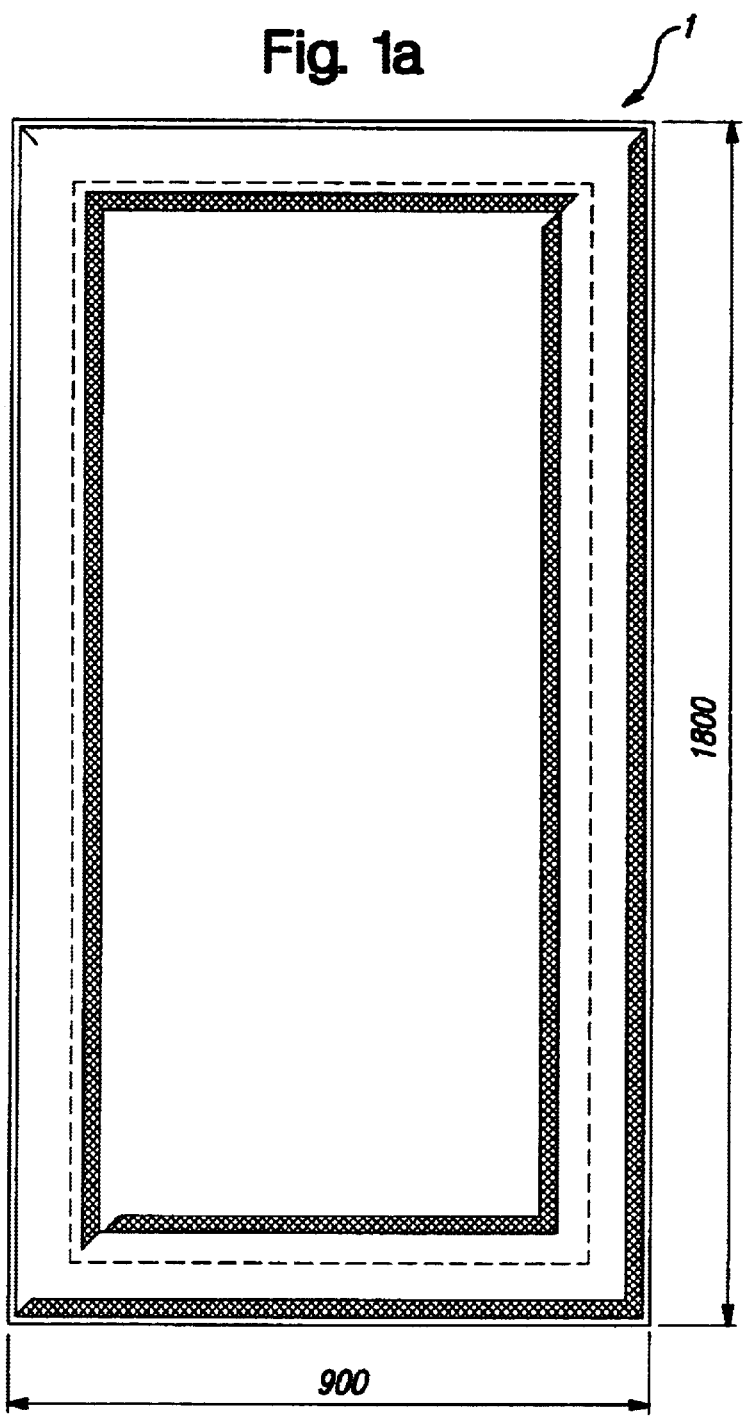

This application is a continuation-in-part of Ser. No. 09/195,450, filed on Nov. 18, 1998 now U.S. Pat. No. 6,258,435.

BACKGROUND OF THE INVENTION

The present invention relates to hygiene mats on which users, e.g. visitors, can disinfect the soles of their shoes or boots, before they enter into a barn or the like.

At many farms it is common practice to try to exclude contamination through shoes and/or boots by placing open containers with disinfection fluids at the entrances. Visitors can disinfect their shoes and boots by 'dipping' their feet into the container filled with disinfection liquid. Many of these containers are cut out plastic jerrycans which contain variable quantities of liquid that pollute quickly and in which visitors are alomost unable to disinfect their shoes or boots without running the risk of getting wet feet.

SUMMARY OF THE INVENTION

The invention relates to a combination of a liquid retaining mat, which is substantially fully surrounded by a wear resistant, permeable fabric material, fitted in a waterproof sleeve to prevent leaking of the liquid into the environment.

In particular, the hygiene mats according to the present invention comprise an absorbing mat which is covered on substantially all sides by a protective, woven, permeable polypropylene material and supplied with a waterproof sleeve which is open on the top side in order to contain disinfecting liquid(s).

The mats can be manufactured in different sizes for different applications to replace the known open 'footbaths', pieces of carpet or foamrubber.

Based on the above principle, the present invention aims to provide for more than one application.

The invention aims to be a quality medium to disinfect the shoes or boots of visitors to the premises, or alternatively the equipment, like the wheels of farm transport means, carts, forklifttrucks and furthermore the wheels of cars and lorries. In this connection, the invention aims to provide a reservoir for disinfecting liquid, without hard, upstanding edges, where an easy application and passage is combined with a longer contact between the object to disinfect and the disinfecting liquid. In the case of persons using the hygiene mats, said longer contact is caused by the fact that a user can stand on the mat with both feet, without liquid running over and into his shoes. In case the mats are being used by transport means, it is prevented that said means have to pass over elevations or edges in or on the floor.

The invention also aims to be an alternative to the partial care of the feet or claws of farm animals like cattle and sheep. In this case the mat is provided with a caring or disinfecting, or another purpose serving, product. The animals are made to walk over the mat and consequently come into contact with the product contained in the mat.

The latter purpose of the invention is advantageous as animals have a natural dislike for open surfaces of water and tend to jump over such surfaces or containers providing such surfaces. Furthermore they have the reflex to manure in the resrvoir or water surface when they are forced to pass it.

BRIEF DESCRIPTION OF THE PREFERRED EMBODIMENTS

Figure 1B:
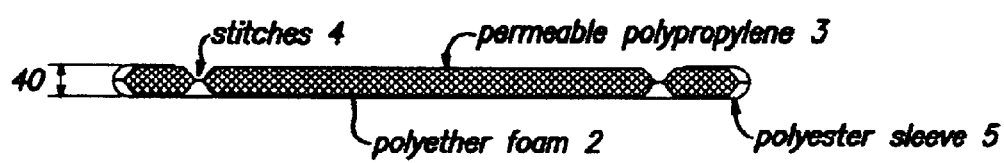

The above and other objects and advantages of the present invention will become apparent from the following description when read in conjunction with the accompanying drawings, wherein:

FIG. 1 shows schematically a top view of the hygiene mat according to the present invention in a first embodiment; and FIG. 2–FIG. 7 show hygiene mats according to further embodiments.

DETAILED DESCRIPTION OF THE PREFERRED EMBODIMENTS

As mentioned in the above, the mats according to the invention may be used for different applications, namely as:

1. disinfecting mat for persons;
2. disinfecting mat for equipment; and
3. claw mat for animals.

Depending on the application, the measurements of the mats will vary. The construction principle of the mat according to the invention is as follows. The mat 1 comprises a liquid retaining core, in particular a polyether core, indicated by reference numeral 2, which is surrounded by a permeable material layer 3 that prevents polution and wear of the core and therefore increases the life thereof. Preferably, the permeable material layer 3 is made of polypropylene.

The polyether core, or polyether foam, 2 advantageously comprises polyether SG 20 to SG 40, and preferably has a thickness of 20 mm–80 mm. The permeable protection of polypropylene preferably has a density of 265 g/m$^2$ and comprises quality 24119 from Nicolon TenCate®.

In order to improve the strength of the construction, the mat is preferably stitched at about 10–15 cm from the edges thereof. Said stitches are indicated with reference numeral 4.

The core 2, surrounded with the material layer 3, is provided with a cover 5 which is meant to function as a container restraint for a liquid to be contained in the core.

Preferably, the cover 5 comprises a double coated polyester material. Preferably, the density of the polyester material is 650 g/m$^2$.

As shown in the drawings, the cover 5 covers the bottom and the sides of the core, and covers only partially the top thereof. A person using the mat will step on said mat in the non-covered area and will come into contact with the liquid retained in the core thereof. As mentioned in the above, the liquid may be a disinfecting liquid or any other liquid, such as a caring liquid.

Because of the close surrounding of the cover 5 on the core 2 with the material layer 3, the disinfecting liquid is pushed upwards whenever the mat is being stepped on. The location where a person puts his feet down on the mat will be compressed and liquid will flow immediately to this lowest point and will surround the shoes of boots of said person. In the case of an animals, the claws of said animal will be surrounded by the liquid and in the case of transport equipment, the wheels thereof will be surrounded.

Figure 2A:
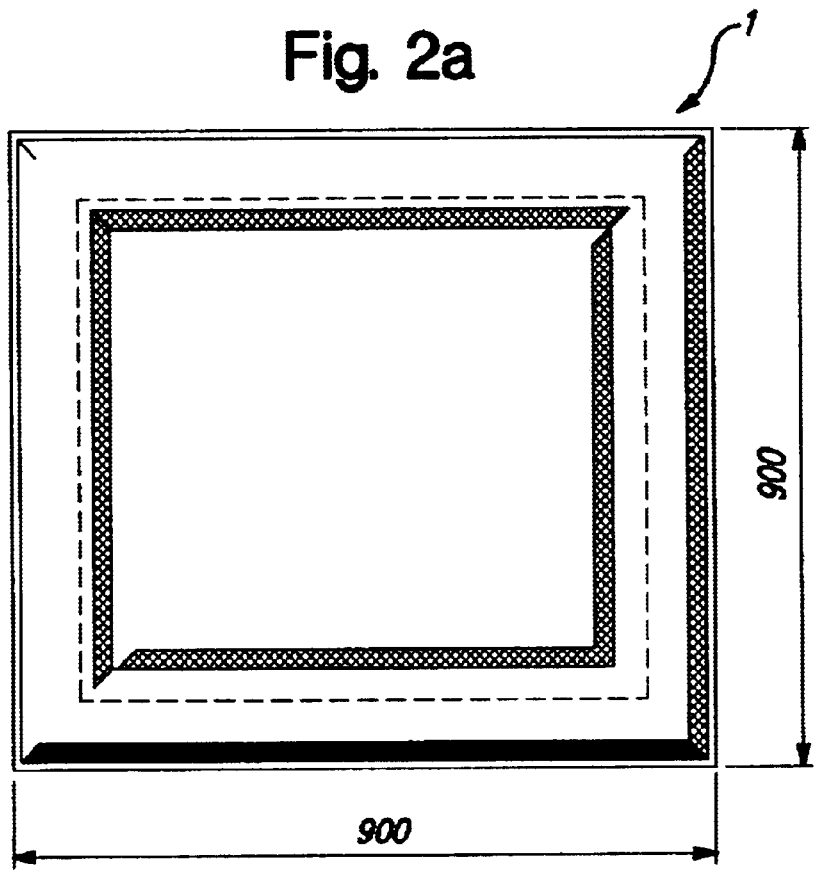
Figure 2B:
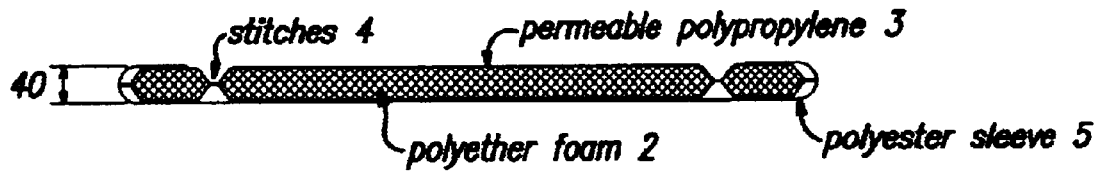
Figure 3A:
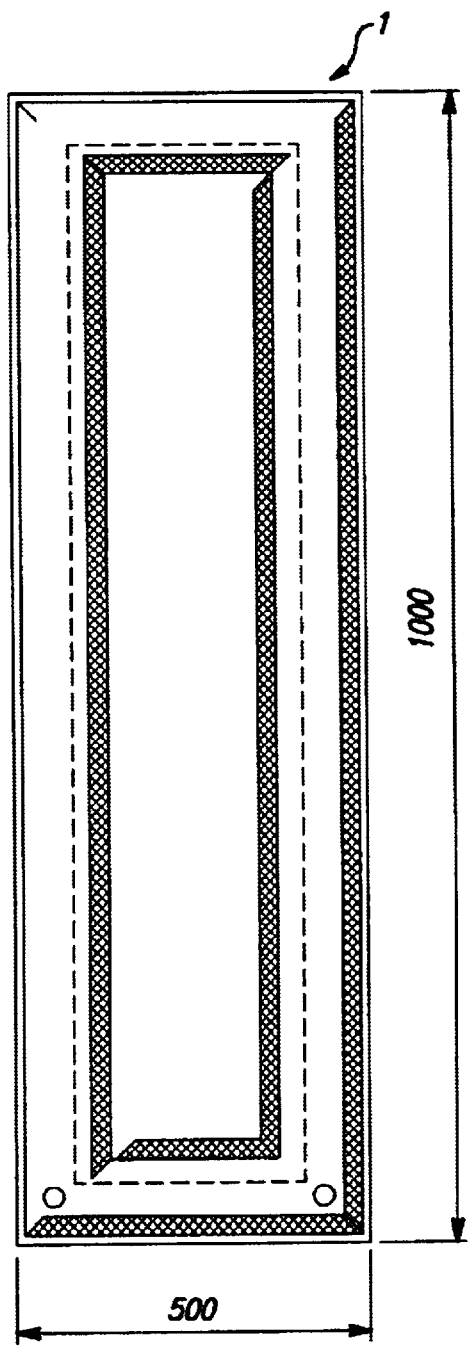
Figure 3B:
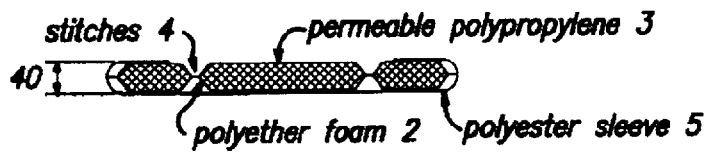
Figure 4A:
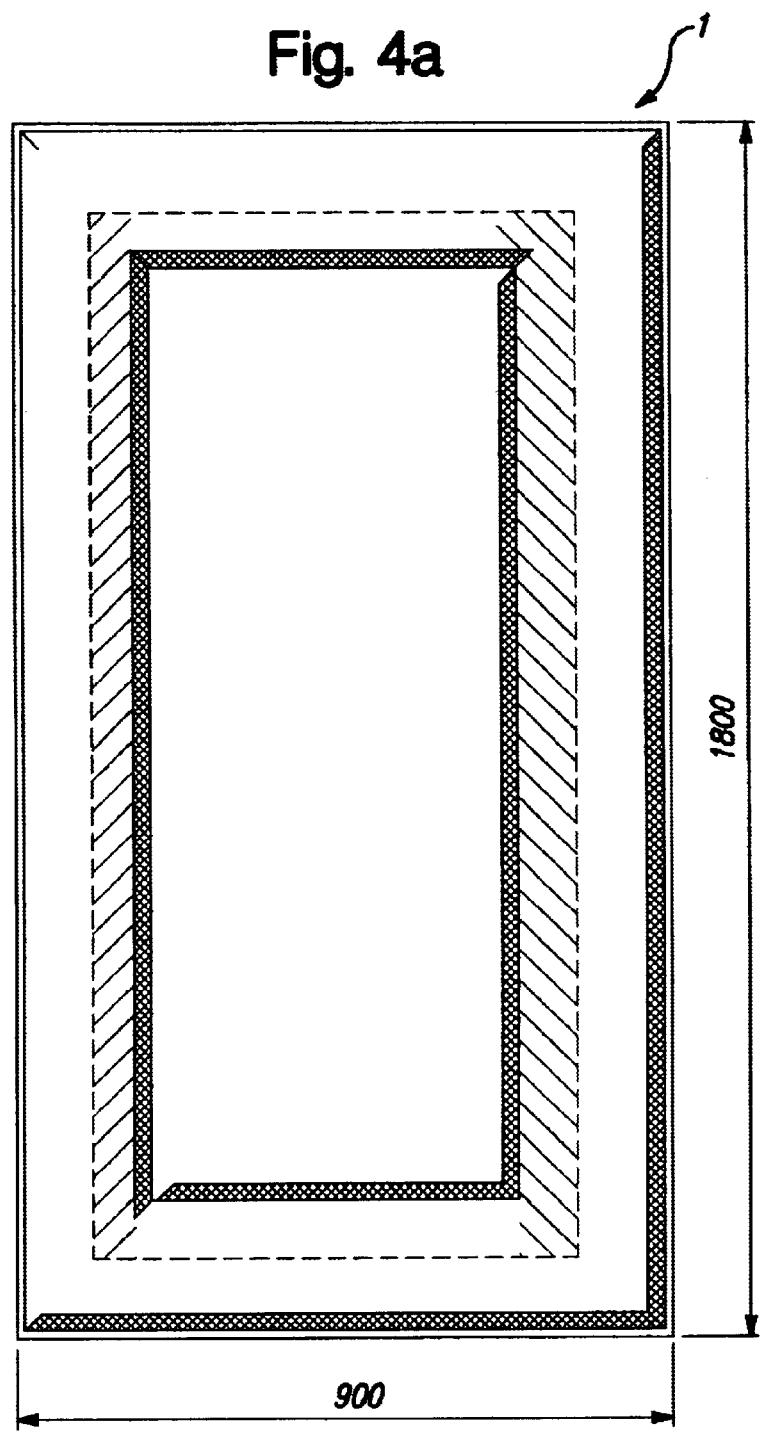
Figure 4B:
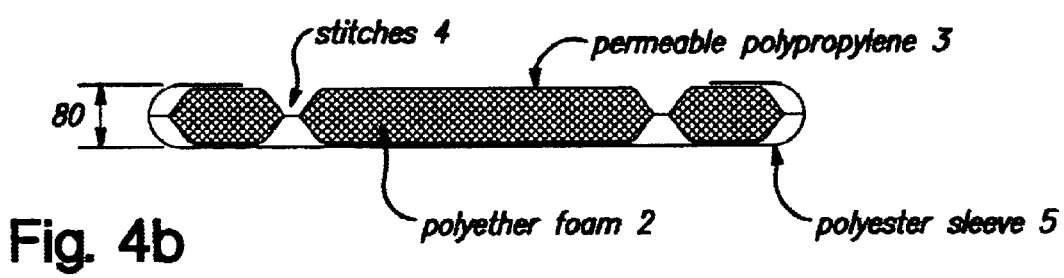
Figure 5A:
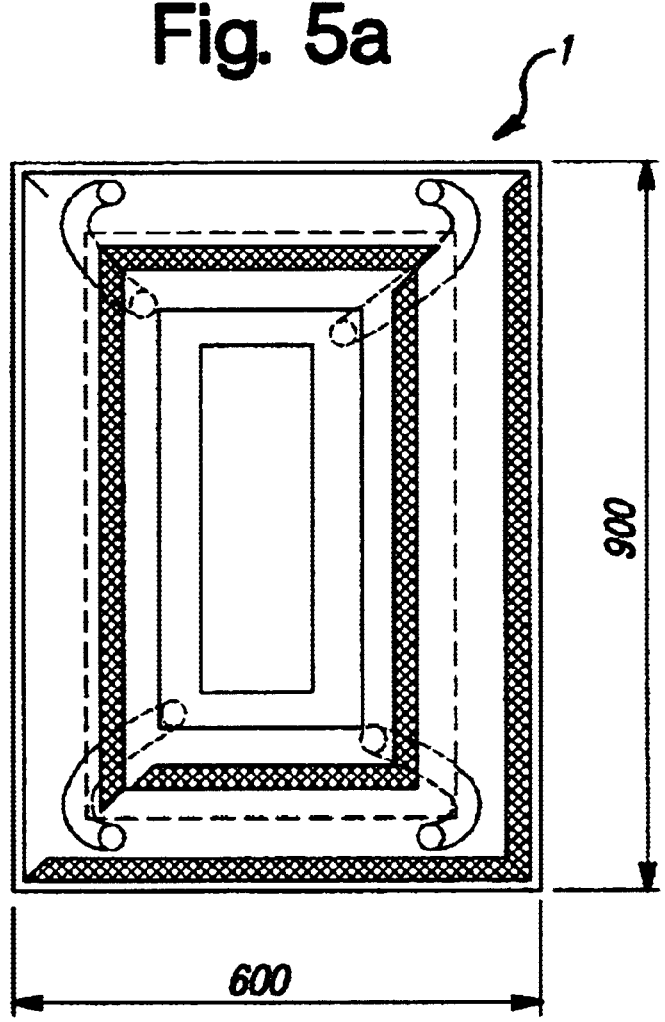
Figure 5B:
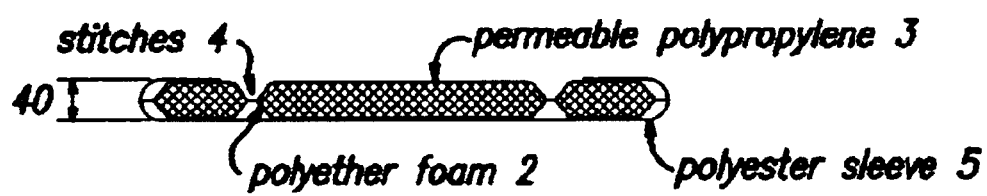
Figure 6A:
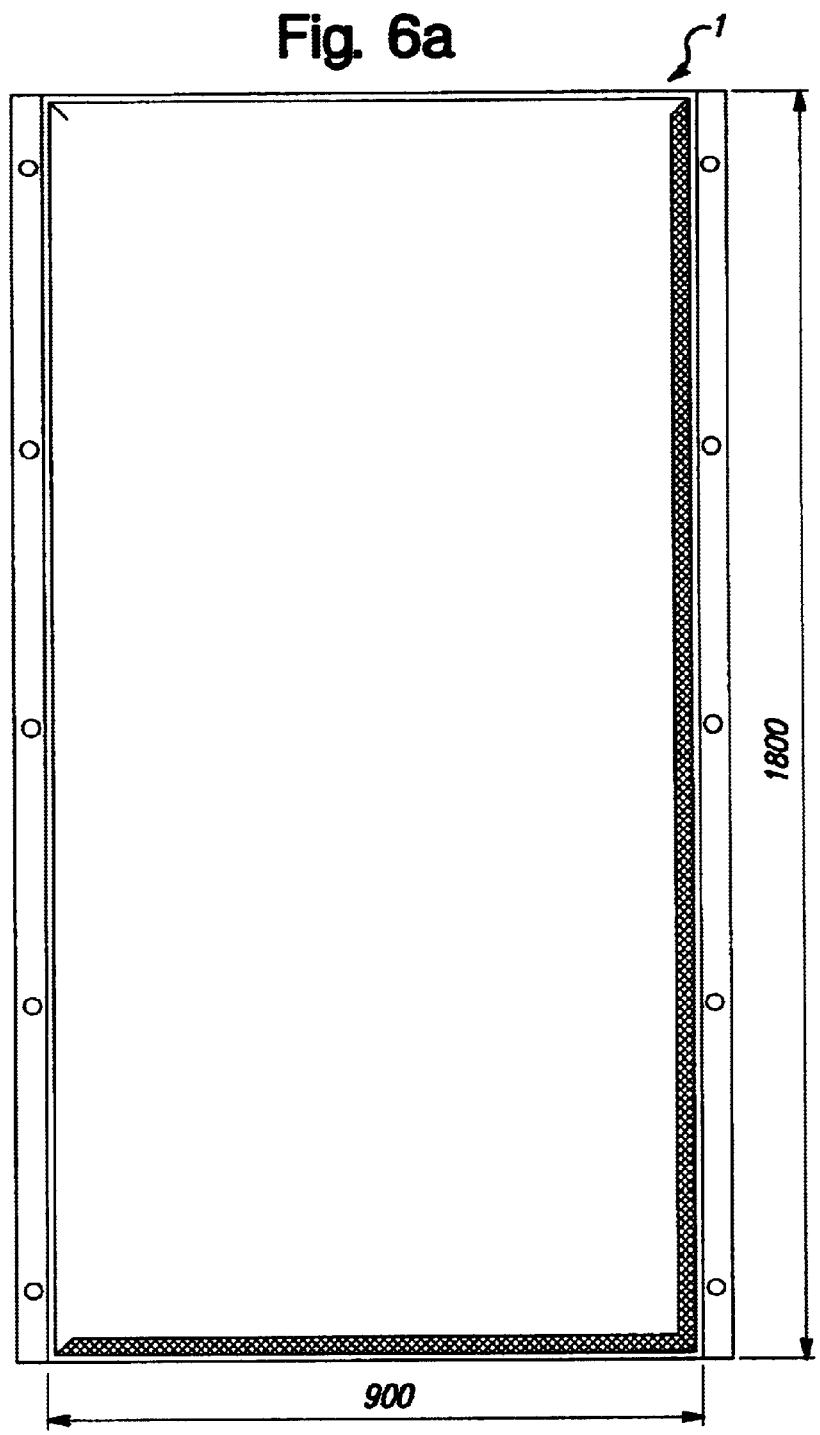
Figure 6B:
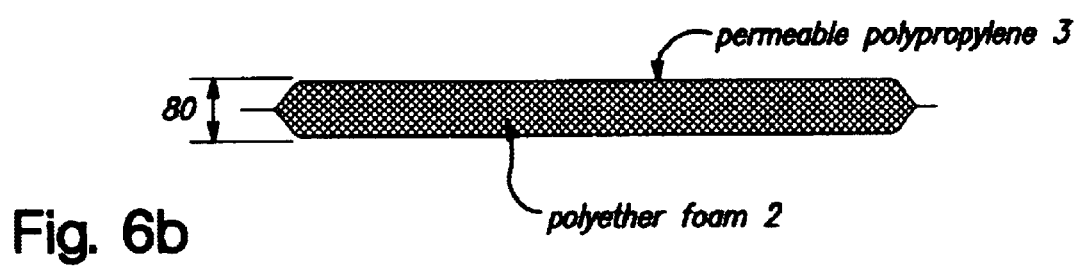
Figure 7A:
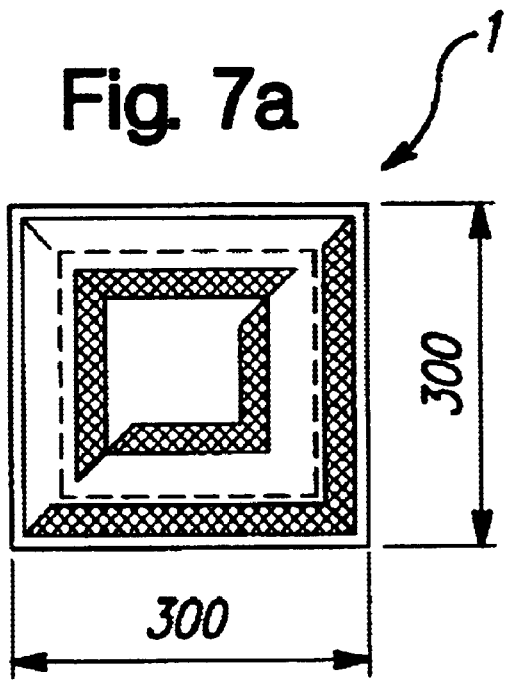
Figure 7B:
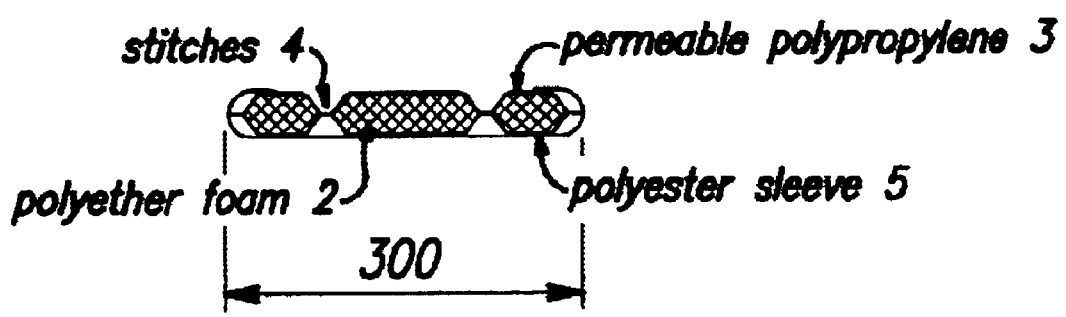

The measurements of the mats according to FIGS. 1–7 vary and are as follows:

FIG. 1 1800×900×40 mm (l×w×h)
FIG. 2 900×900×40 mm (l×w×h)
FIG. 3 1800×500×40 mm (l×w×h)
FIG. 4 1800×900×80 mm (l×w×h)
FIG. 5 900×600×40 mm (l×w×h)
FIG. 6 1800×900×80 mm (l×w×h)
FIG. 7 300×300×32 mm (l×w×h)

Further embodiments of the present invention are also possible. The sleeve may further include a seal in the edge of the sleeve along one or more sides, preferably the shorter sides, such as shown in FIG. 2. The seal may be in the form of a piece of foam rubber, optionally recycled foam rubber. The seal causes a more narrow connection between the sleeve and the core which may help to prevent animals from stumbling when they step forward to leave the mat at the front side or when they step backward to leave the mat at the back side again.

The sleeve may also be provided with eyes (such as shown in FIG. 3) or a suspension frame, such as a tape. This allows the mat to be suspended, which simplifies storage, drying, and transport.

The core may further include a strip of stiff material (FIG. 4), such as polyvinylchloride (PVC). The strip may be placed inside the core along one or more sides, preferably one or both of the long sides, to increase stiffness of the core. This prevents the core from "jumping" out of the sleeve, which might otherwise occur under strenuous use.

With reference to FIG. 5, the mat may also include a reservoir sealed at a bottom of the sleeve to store liquid. The reservoir may be filled with foam. Liquid will be sucked into the reservoir when the core is empty, optionally through use of a piston mechanism,. When the core is depressed, liquid will be sprayed from the reservoir via a pipe made from a soft material onto the object being cleaned, such as the claw of an animal.

In another embodiment, a soft bin is formed by sealing within the total edge of the sleeve a filling of 4–8×6 cm over which a stiff fabric, such as polypropylene, preferably a so called "trampoline" fabric, has been stretched by stitching or sealing it at one side and using an attachment mechanism, such as hook and loop tape, at the other side. This embodiment provides the advantages of greater ease in cleaning and transport as there is no foam rubber, and the likelihood of stumbling is minimized. Of course, such a soft bin may also be used without the stiff cover fabric as a bin to drive or walk through, or in combination with the core described above.

What is claimed is:

1. A mat comprising:

a core constructed and arranged to be able to retain a liquid;

a permeable material surrounding the core; and a waterproof sleeve, the core and the permeable material being fitted within the waterproof sleeve, the waterproof sleeve covering a bottom, sides, and a portion of a top of the core;

wherein when the sleeve contains a liquid and the mat is depressed, the waterproof sleeve prevents leakage of the liquid.

2. The mat of claim 1, further comprising a seal in an edge of the sleeve along one or more sides of the sleeve.

3. The mat of claim 1, wherein the sleeve further comprises a suspension mechanism.

4. The mat claim 1, wherein the core further comprises a strip of stiff material inside the core along at least one side of the core.

5. The mat of claim 1, further comprising a reservoir disposed at a bottom of the sleeve and a spray mechanism connected to the reservoir so that when the core is depressed, liquid will be sprayed from the reservoir onto an object on the mat.

* * * * *